United States Patent [19]

Dunlavy

[11] Patent Number: 5,658,234

[45] Date of Patent: Aug. 19, 1997

[54] METHOD FOR TREATING TUMORS

[75] Inventor: John Harold Dunlavy, Colorado Springs, Colo.

[73] Assignees: J. D. Technologies, Inc., Colorado Springs, Colo.; Haynes and Boone, L.L.P., Dallas; Donald M. Feferman, Corpus Christi, both of Tex.

[21] Appl. No.: 505,872

[22] Filed: Jul. 24, 1995

[51] Int. Cl.$^6$ .............................. A61M 31/00; A61N 2/00
[52] U.S. Cl. .................................................. 600/9; 604/49
[58] Field of Search ........................ 600/9–10, 13–14; 604/49, 51; 128/898; 607/103

[56] References Cited

U.S. PATENT DOCUMENTS

| | | |
|---|---|---|
| Re. 32,066 | 1/1986 | Leveen . |
| 3,991,770 | 11/1976 | LeVeen . |
| 4,106,488 | 8/1978 | Gordon . |
| 4,154,246 | 5/1979 | LeVeen . |
| 4,230,129 | 10/1980 | LeVeen . |
| 4,303,636 | 12/1981 | Gordon . |
| 4,469,103 | 9/1984 | Barrett . |
| 4,622,952 | 11/1986 | Gordon . |
| 4,662,359 | 5/1987 | Gordon . |
| 4,690,130 | 9/1987 | Mirell . |
| 4,702,262 | 10/1987 | Andersen et al. . |
| 4,767,611 | 8/1988 | Gordon . |
| 4,800,899 | 1/1989 | Elliott . |
| 5,197,940 | 3/1993 | Sievert et al. . |
| 5,466,576 | 11/1995 | Schulz et al. . |

OTHER PUBLICATIONS

Widder, Kenneth J. et al, "Experimental Methodsin Cancer Therapeutics" J. of Pharm. Sciences, vol. 71 No. 4 Apr. 1982 pp. 379–387.

*Primary Examiner*—Mark Bockelman
*Assistant Examiner*—Ellen Tao
*Attorney, Agent, or Firm*—Haynes and Boone, L.L.P.

[57] ABSTRACT

This invention relates generally to a method for treating a tumor comprising the steps of selecting a target substance which has at least one component with an atomic or molecular resonance frequency or frequencies different from the atomic, molecular or cellular resonant frequencies of normal cells, locating or depositing the target substance within the tumor, and irradiating the target substance with electromagnetic wave energy at a frequency or frequencies corresponding to the atomic or molecular resonance of the component such that the component absorbs energy from the electromagnetic wave, resulting in the release of heat sufficient to destroy, terminate or slow the growth of the tumor without adversely affecting the viability of normal cells.

7 Claims, No Drawings

METHOD FOR TREATING TUMORS

TECHNICAL FIELD

This invention relates to a method of treating tumors, and more particularly, to a method of treating benign and malignant tumors afflicting human beings by utilizing electromagnetic energy.

BACKGROUND OF THE INVENTION

Considerable research within many medical research laboratories throughout the world has been directed towards developing effective non-invasive treatments for destroying and arresting the growth of both benign and malignant forms of tumors. However, none of the treatments thus far devised have demonstrated acceptable levels of tumor cell necrosis during either clinical trials or general practice in the field of oncology.

For example, one method for treating tumors that has been tried, called brachytherapy, involves first injecting microscopic clumps of the protein albumin directly into the tumor by means of a needle. A suitable quantity of radioactive phosphorous is then added through the same needle. During the first few hours, the albumin clogs the capillaries within the tumor, preventing the release of the phosphorous to other parts of the body. Since tumor cells quickly take up and use the phosphorous, its radioactivity selectively kills them without damaging normal cells in other parts of the body. By the time the capillaries become unclogged, all or most of the radioactive phosphorous has been absorbed by the cells comprising the tumor, leaving little to escape into adjacent tissue. However, this method of treatment is difficult to implement and always carries the danger of radioactive material escaping into healthy parts of the body where it might produce serious damage.

Another method for treating tumors that is currently being evaluated by medical researchers makes use of a substance called telomerase, an enzyme that tumor cells produce and require to remain alive, but which normal body cells (except for sperm) neither produce nor require. This unique property of telomerase has prompted attempts to develop a drug that will block the action of the enzyme sufficiently to either inhibit the growth of new tumor cells or cause the death of older ones. Telomerase is an example of a class of substances that are often referred to as being "tumor-specific" because they are needed and/or used by tumor cells in differentially larger amounts than by normal healthy cells of the body.

Yet another method for treating tumors is disclosed in U.S. Pat. No. 4,622,952 issued to Robert T. Gordon (hereinafter "Gordon") which attempts to take advantage of the observed differential heat sensitivity of tumor cells and normal cells. As disclosed in Gordon, it is well known that upon elevating the temperature of tumor and normal cells, tumor cells are killed at a lower temperature than normal cells. In Gordon a method was proposed to use electromagnetic energy to elevate the temperature of tumor cells or tissues, relative to normal cells, to kill the tumor cells without seriously affecting normal cells.

Gordon suggested that, as a result of certain physical differences between normal and tumor cells and tissues, tumors exhibit different cellular and tissue resonant frequencies from normal cells and tissues. Gordon proposed that by determining the cellular resonant energy absorption frequency of tumor cells and tissues in a patient, and exposing the patient to an electromagnetic energy field having the same resonant frequency as the tumor cells or tissues, the tumor cells or tissue would absorb energy causing the intracellular temperature to differentially rise compared to the normal cells and tissues. By controlling the amount of electromagnetic energy delivered, the temperature of the tumor cells and tissues could be raised to a degree which causes their destruction while leaving normal cells unaffected.

Gordon additionally disclosed alteration of the magnetic susceptibility and resonant absorption frequencies of cell and tissue structures by injecting a magnetically excitable material, such as FeOOH, into the cell structure. The FeOOH absorbed in the cell structure could then be magnetically excited by a 450 kilohertz magnetic field to cause biophysical alterations in the cell structure. However, because the determination of the resonant frequencies of various cell and tissue structures has been difficult to obtain, and the resonant frequencies of normal cell structures are frequently too close to those of the tumorous cells to avoid harming the normal cells, the method proposed by Gordon has found little practical use to date.

Despite the wide-ranging and expensive efforts expended in researching, developing and evaluating new treatments and cures for tumors and cancers, no truly significant advances or completely satisfactory treatments have thus far been achieved.

SUMMARY OF THE INVENTION

It is therefore an object of the present invention to provide a satisfactory treatment for both benign and malignant tumors which avoids the disadvantages and dangers of the prior treatments discussed above, especially with respect to the use of radioactive substances.

It is a further object of the present invention to provide a treatment of the above type which utilizes differential heat sensitivity between tumor cells and normal, healthy human cells.

Another object of the present invention is to provide a treatment of the above type in which a tumor-specific, or target, substance is introduced to the tumor, which target substance selectively accepts electromagnetic wave energy by atomic or molecular resonance, as opposed to cellular or tissue resonance, to differentially raise the temperature of adjacent tumor cells relative to normal cells and thus destroy them without unduly affecting the viability of the normal cells.

A still further object is to provide a treatment that makes use of the above treatment means but is preceded by an injection into the tumor of a protein such as albumin to block the capillaries within the tumor to prevent the escape of any target substance into the body of the patient which might produce adverse effects when coming into contact with normal cells outside the area of the tumor.

Towards the fulfillment of these and other objects, the subject treatment requires the selection of a target substance which can be either native to the tumor or injected into it by suitable means and which target substance must necessarily selectively accept and absorb certain electromagnetic wave energy at one or more frequencies corresponding to its atomic or molecular resonance, which must also be suitably different in frequency from the atomic, molecular and cellular resonances of normal cells. By irradiating the area of the tumor with electromagnetic wave energy of suitable intensity at one or more of these frequencies of resonance, the temperature of the target substance is caused to rise within the tumor until necrosis or termination of growth is achieved, while leaving adjacent normal cells unaffected.

DESCRIPTION OF THE PREFERRED EMBODIMENT

Research has disclosed that the viability and reproductive properties of tumor cells are greatly diminished at temperatures modestly higher than the average body temperature of 98 degrees (F.), whereas normal cells and healthy tissue can withstand much higher temperatures without incurring serious or permanent damage. Indeed, locally contained temperatures of only about ten to twelve degrees (F.) above the normal body temperature are generally sufficient to produce necrosis of most tumor cells within a relatively short period of time. This differential sensitivity to heat, therefore, provides a means for selectively destroying tumor cells, both benign and malignant, without seriously affecting normal cells and tissue.

It is well known that every atom and molecule has at least one frequency at which it exhibits a resonance to incident electromagnetic energy. The frequencies that produce atomic and molecular resonance are exceedingly high, generally in the microwave range, relatively easy to determine, and are highly specific from one atom or molecule to another. When subjected to the energy of an external electromagnetic field at their specific frequency or frequencies of resonance, atoms and molecules selectively absorb energy from the electromagnetic field. The absorption of this energy causes either the electron orbits of the atoms to change or the atoms or molecules to vibrate.

When the electrons undergo orbital changes, the result is generally the production of ultra-violet radiation. However, when atomic or molecular vibration modes are induced by the resonance condition, energy is usually released in the form of heat by infra-red or far infra-red electromagnetic waves. By properly exciting a given vibrational mode at the atomic or molecular resonant frequency of an atom or molecule, intense levels of heat can be generated and released into adjacent materials.

Thus, microwave radiation can be used to produce significant amounts of heat within any material or substance comprised of atoms or molecules which exhibit a suitable atomic or molecular resonance. The important aspect of this type of heating is that it is differentially and selectively produced within specific atoms or molecules only by electromagnetic radiation at the exact frequency at which they exhibit resonance. One example of a practical use of this property is the "microwave oven" which employs electromagnetic (microwave) radiation at or near the resonant frequency of the water molecule ($H_2O$) at 2450 MHz to heat or cook any food containing a relevant percentage of water. When the food is exposed to electromagnetic radiation at 2450 MHz, energy is absorbed by the water molecules and released in the form of heat which is transferred to surrounding material in the food. Foods containing little or no water are virtually unaffected by the microwave radiation within the oven.

Thus according to the present invention, the simplest form of treatment would begin with the choice of a proper and suitable target substance. This target substance might be either native to the tumor cells, such as telomerase, or one injected by suitable means into the area invaded by the tumor cells (which could also include a substance native to the tumor cells, such as telomerase). The target substance chosen must exhibit one or more frequencies of atomic or molecular resonance at which it efficiently absorbs energy from a properly directed incident electromagnetic wave of suitable intensity at the same frequency or frequencies and converts a major portion of the absorbed energy into heat.

Further, the frequencies of atomic or molecular resonance exhibited by the target substance must be sufficiently different from the like resonances exhibited by all elements and components of normal cells. Upon determination of a native target substance, or injection of a non-native target substance into the tumor, the area of the tumor is subjected to electromagnetic waves of suitable intensity at the target substance's atomic or molecular resonant frequency. The target substance alone absorbs the electromagnetic energy which is released in the form of heat to the adjacent tumor cells, thus causing their necrosis, without seriously affecting normal cells.

For certain applications, an alternate means of using microwave heating to treat tumors according to the present invention would include first injecting a suitable protein such as albumin into the tumor to clog internal capillaries, followed by an injection of a suitable target substance such as a non-radioactive, non-toxic molecule into the same area. This prevents any consequential leakage of the target substance into nearby healthy tissue before most of it has been absorbed by the tumor cells. The tumor is then selectively exposed to a suitable level of electromagnetic radiation at one or more frequencies which coincide with the atomic or molecular resonance or resonances of the target substance. When so irradiated, the relevant atoms or molecules of the target substance alone absorb energy from the electromagnetic waves and thereby heat up to a level that is lethal to the tumor cells. Since the target substance only harms adjacent tissue when selective electromagnetic radiation is applied, this method does not suffer from the potential harmful affects which can be caused by a radioactive substance released into the body after the capillary clogging action of albumin or another protein has subsided.

A further embodiment of the present invention would use a "tumor-specific" target substance or enzyme, such as telomerase, wherein the given target substance contains molecules which exhibit a resonance at one or more frequencies that, when radiated from a suitable source of electromagnetic energy at such a frequency or frequencies, selectively heat up and attain a much higher (and more lethal) temperature than the surrounding normal healthy tissue. The use of such a "tumor-specific" target substance has the advantage, of course, of naturally confining the target substance to the area of the body under treatment.

Thus, it may be seen that the present invention enjoys several advantages over existing procedures. For example, it enables tumors to be treated and destroyed while avoiding the disadvantages and dangers of the prior treatments discussed above. This principle is significant because "microwave heating" of a tumor-specific substance or an "injectable substance" provides a superior and far less dangerous method of treatment, if properly implemented, than the use of a radioactive substance, as described above. Further, because the present invention relies on atomic or molecular resonant frequencies, as opposed to cellular or tissue resonant frequencies, the above-discussed problems associated with Gordon have been eliminated.

One example of a suitable tumor specific substance for the treatment of tumors in the human thyroid gland is iodine. Iodine is differentially absorbed by the human thyroid gland and can be intravenously injected into an individual inflicted with a thyroid tumor. After it has been determined that the majority of the iodine has become resident in the thyroid, the tumorous region is selectively irradiated with electromagnetic waves of appropriate intensity at the specific resonant frequency of iodine. The iodine thereby develops sufficient heat to selectively destroy the tumor cells, without adversely affecting nearby healthy tissue. This is possible because the healthy cells and tissue possess a tolerance to levels of heat that are sufficient to cause necrosis of tumor cells.

A latitude of modification, change and substitution is intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. A method for treating tumors within a subject's living tissue, the method comprising the steps of:

selecting a target substance having at least one component with an atomic or molecular resonance frequency or frequencies different from the atomic, molecular or cellular resonant frequencies of normal cells;

depositing said target substance within said tumor; and irradiating said target substance with electromagnetic wave energy at a frequency or frequencies corresponding to the atomic or molecular resonance of said at least one component such that said component absorbs energy from said electromagnetic wave, resulting in the release of heat sufficient to destroy, terminate or slow the growth of said tumor without adversely affecting the viability of said normal cells.

2. The method of claim 1, wherein said selecting step further comprises selecting a target substance that is non-radioactive and non-toxic to said normal cells.

3. The method of claim 1, further comprising the step of:

introducing a substance into said tumor, prior to said depositing step, to clog relevant capillaries in said tumor to retain said target substance within said tumor during said irradiation step.

4. The method of claim 3 wherein said substance is albumin.

5. A method for treating tumors within a subject's living tissue, the method comprising the steps of:

selecting a target substance having at least one component with an atomic or molecular resonance frequency or frequencies different from the atomic, molecular or cellular resonant frequencies of normal cells, and which selectively attaches to, is absorbed by or is otherwise used by said tumor;

intravenously injecting said target substance into said subject such that said target substance attaches to, is absorbed by or is otherwise used by said tumor; and irradiating said target substance with electromagnetic wave energy at a frequency or frequencies corresponding to the atomic or molecular resonance of said at least one component such that said component absorbs energy from said electromagnetic wave, resulting in the release of heat sufficient to destroy, terminate or slow the growth of said tumor without adversely affecting the viability of said normal cells.

6. The method of claim 5 wherein said target substance and said component are iodine.

7. The method of claim 5 wherein said target substance is telomerase.

* * * * *